US010076596B2

(12) United States Patent
Schima et al.

(10) Patent No.: US 10,076,596 B2
(45) Date of Patent: Sep. 18, 2018

(54) CANNULA TIP FOR USE WITH A VAD

(71) Applicant: HeartWare, Inc., Miami Lakes, FL (US)

(72) Inventors: Heinrich Schima, Vienna (AT); Martin Stoiber, Vienna (AT); Georg Wieselthaler, Vienna (AT); Zeno Deckert, Vienna (AT)

(73) Assignee: HeartWare, Inc., Miami Lakes, FL (US)

( * ) Notice: Subject to any disclaimer, the term of this patent is extended or adjusted under 35 U.S.C. 154(b) by 539 days.

(21) Appl. No.: 14/703,122

(22) Filed: May 4, 2015

(65) Prior Publication Data

US 2015/0231317 A1    Aug. 20, 2015

Related U.S. Application Data

(63) Continuation of application No. 12/460,281, filed on Jul. 16, 2009, now Pat. No. 9,050,418.
(Continued)

(51) Int. Cl.
*A61M 37/00* (2006.01)
*A61M 1/10* (2006.01)
*A61M 1/12* (2006.01)

(52) U.S. Cl.
CPC .......... *A61M 1/1008* (2014.02); *A61M 1/122* (2014.02)

(58) Field of Classification Search
CPC .............................. A61M 1/008; A61M 1/122
(Continued)

(56) References Cited

U.S. PATENT DOCUMENTS 4,639,252 A   1/1987  Kelly et al.
5,562,606 A   10/1996 Huybregts et al.
(Continued)

OTHER PUBLICATIONS

Partial European Search Report in EP09798302.7, dated Nov. 3, 2016, 8 pages.
(Continued)

*Primary Examiner* — Philip R Wiest
(74) *Attorney, Agent, or Firm* — Christopher & Weisberg, P.A.

(57) ABSTRACT

The present invention includes various embodiments of methods of circulating blood in a mammalian circulatory system, and various blood circulation assemblies adapted to perform such circulation. In one embodiment of the present invention, a blood circulation assembly includes a blood circulation device having an inlet and a discharge; a first cannula including a proximal portion in communication with the inlet, the proximal portion having a wall extending around a first longitudinal axis and having outer and inner faces, said inner face defining a bore, and a distal portion including an outer face tapering distally toward said axis and at least two openings extending from said outer face and merging with one another to form a hollow space within said distal portion, said hollow space communicating with said bore of said proximal portion; and a second cannula including a proximal portion in communication with the discharge, the proximal portion having a wall extending around a first longitudinal axis and having outer and inner faces, said inner face defining a bore, and a distal portion including an outer face tapering distally toward said axis and at least two openings extending from said outer face and merging with one another to form a hollow space within said distal portion, said hollow space communicating with said bore of said proximal portion.

13 Claims, 4 Drawing Sheets

Related U.S. Application Data

(60) Provisional application No. 61/135,004, filed on Jul. 16, 2008.

(58) Field of Classification Search
USPC .............................................. 604/4.01–6.16
See application file for complete search history.

(56) References Cited

U.S. PATENT DOCUMENTS

| | | | |
|---|---|---|---|
| 5,769,828 A | 6/1998 | Jonkman | |
| 5,817,071 A | 10/1998 | Dewindt et al. | |
| 6,007,478 A | 12/1999 | Siess et al. | |
| 6,059,760 A * | 5/2000 | Sandmore | A61M 25/007 604/264 |
| 6,106,494 A | 8/2000 | Saravia et al. | |
| 6,146,371 A | 11/2000 | DeWindt et al. | |
| 6,447,484 B1 | 9/2002 | Briscoe et al. | |
| 6,461,321 B1 * | 10/2002 | Quinn | A61M 25/003 604/266 |
| 6,645,194 B2 | 11/2003 | Briscoe et al. | |
| 6,926,662 B1 | 8/2005 | Aboul-Hosn et al. | |
| 6,942,611 B2 | 9/2005 | Siess | |
| 6,969,379 B1 | 11/2005 | Aboul-Hosn et al. | |
| 6,976,979 B2 | 12/2005 | Lawrence et al. | |
| 7,011,645 B2 | 3/2006 | McGuckin, Jr. et al. | |
| 7,264,606 B2 | 9/2007 | Jarvik et al. | |
| 9,050,418 B2 * | 6/2015 | Schima | A61M 1/3653 |
| 2006/0004316 A1 | 1/2006 | Difiore et al. | |
| 2006/0069299 A1 | 3/2006 | Aboul-Hosn et al. | |
| 2006/0100565 A1 | 5/2006 | Aboul-Hosn | |
| 2006/0100572 A1 | 5/2006 | DiMatteo et al. | |
| 2006/0264801 A1 | 11/2006 | Bolling et al. | |
| 2006/0270962 A1 | 11/2006 | McGuckin et al. | |
| 2007/0197856 A1 | 8/2007 | Gellman et al. | |
| 2008/0114339 A1 | 5/2008 | McBride et al. | |
| 2009/0203957 A1* | 8/2009 | LaRose | A61M 1/101 600/18 |

OTHER PUBLICATIONS

International Preliminary Report on Patentability for PCT/US2009/004109 from the International Searching Authority; dated Jan. 18, 2011.

International Search Report, dated Aug. 19, 2009, for PCT/US09/004109.

MEDTRONIC, Venous Cannulae.

U.S. Appl. No. 61/065,140, filed Feb. 8, 2008.

U.S. Appl. No. 61/198,682, filed Nov. 7, 2008.

Written Opinion of the International Searching Authority dated Aug. 19, 2009 issued by the International Searching Authority (ISA/US) in connection with International Application No. PCT/US09/04109.

\* cited by examiner

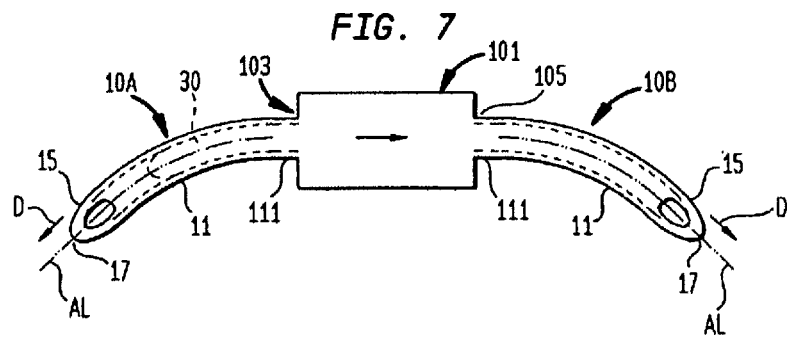
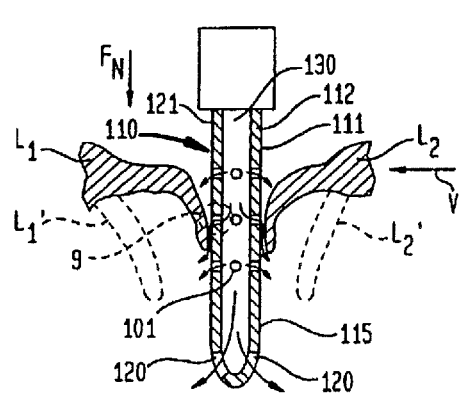
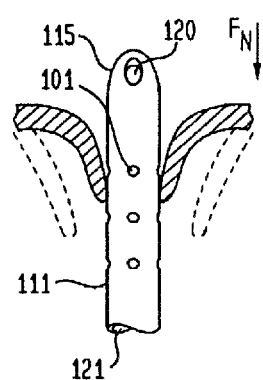
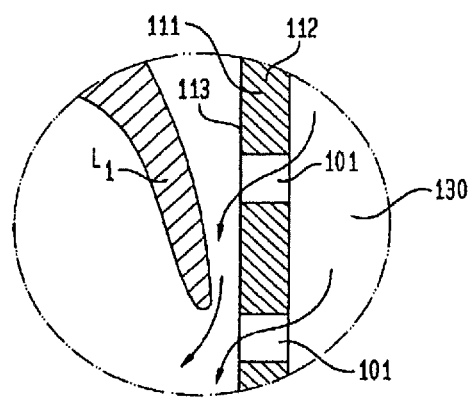

CANNULA TIP FOR USE WITH A VAD

CROSS-REFERENCE TO RELATED APPLICATIONS

The present application is a continuation of U.S. patent application Ser. No. 12/460,281, filed on Jul. 16, 2009, which claims the benefit of the filing date of U.S. Provisional Patent Application No. 61/135,004 filed Jul. 16, 2008, the disclosures of which are incorporated herein by reference.

BACKGROUND OF THE INVENTION

The present invention relates generally to a cannula which may be used, in some embodiments, with a Ventricular Assist Device ("VAD").

In certain disease states, the heart of a human or other mammalian subject lacks sufficient pumping capacity to meet the needs of the body. This inadequacy can be alleviated by providing a mechanical pump referred to as a Ventricular Assist Device ("VAD") to supplement the pumping action of the heart. The intake of the VAD may be equipped with an intake cannula having an interior bore. The VAD and intake cannula may be positioned such that at least a portion of the intake cannula is positioned within a ventricle or atrium. This portion of the intake cannula, typically at or near an end of the cannula, includes an intake region where the interior bore of the cannula communicates with the surroundings. Thus, the VAD can take in blood from within the ventricle.

The discharge of a VAD may be connected to the interior bore of a discharge cannula. The discharge cannula has a discharge region, typically at or near an end of the cannula, where the interior bore of the cannula communicates with the surroundings. The discharge region is positioned in an artery or vein, most commonly in the aorta. Thus, the VAD can discharge blood through the discharge cannula into the artery or vein.

Other arrangements use cannulas with other blood pumping devices in a generally similar fashion. In general, the intake region of an intake cannula, or the discharge region of a discharge cannula, can be positioned within a portion of the circulatory system such as a vein, artery or coronary chamber.

The intake or discharge region of the cannula should resist movement caused by the flow of blood into or out of the cannula. This allows the cannula to remain stable and minimizes or prevents injury to the surrounding tissue, such as the wall or valve of the heart, or blood vessel. It is also desirable to minimize flow resistance through the cannula, and particularly the flow resistance of the intake or discharge region. Moreover, the flow pattern of the blood entering or leaving the cannula should minimize turbulence and eddying, which may destabilize the cannula as well as damage the flowing blood. Additionally, the intake or discharge region should be resistant to accidental blockage or suction which may occur if the intake or discharge region comes in contact with the heart or blood vessel wall. The intake or discharge region should be free of features such as sharp edges or projections which can damage the surrounding tissue. Also, the intake or discharge region should have a shape which can be formed readily. All of these factors, taken together, present a significant engineering challenge. Thus, there has been a need in the art for further improvement in cannula design.

SUMMARY OF THE INVENTION

One aspect of the present invention provides a cannula for use with a blood circulation device such as a VAD, the cannula having a longitudinal axis and proximal and distal directions along the longitudinal axis. The cannula may include a proximal portion having a wall extending around the longitudinal axis and having outer and inner faces. The inner face may define a bore, the proximal portion may have dimensions transverse to the longitudinal axis, and the dimensions may be constant in the proximal and distal directions. Also, the cannula may have a distal portion having an outer face, continuous with the outer face of the proximal portion. The outer face of the distal portion may extend around and along the longitudinal axis, and the outer face of the distal portion may taper distally toward the longitudinal axis. The distal portion may include at least two openings extending from the outer face of the distal portion. The openings desirably merge with one another within the distal portion. The openings may communicate with the bore of the proximal portion. At least a portion of each opening may be axially aligned with the bore, such that a straight line extending through the opening parallel to the longitudinal axis extends, unobstructed by any part of the cannula, into the bore.

As further discussed below, certain embodiments of the cannula according to this aspect of the invention provide a desirable combination of low flow resistance, stability in use, minimal damage to the blood and other desirable properties.

Another aspect of the invention also provides a cannula for use with a blood circulation device. The cannula according to this aspect of the invention desirably has a longitudinal axis and proximal and distal directions along the axis. The cannula according to this aspect of the invention desirably includes a proximal portion having a wall extending around the longitudinal axis and having outer and inner faces, said inner face defining a bore, as well as a distal portion having one or more openings communicating with the bore of the proximal portion. The cannula according to this aspect of the invention preferably has ports extending through the wall of the proximal portion and communicating with the bore in the proximal portion. The ports preferably have aggregate resistance to fluid flow which is substantial in comparison to the aggregate fluid flow resistance of the openings. In a method according to yet another aspect of the invention, the cannula is positioned to extend through a valve of the circulatory system of a mammalian subject such as a human, and blood is supplied to the bore. A substantial portion of the blood, and desirably a majority of the blood passes out of the cannula through the opening. However, some of the blood passes out of the cannula through the ports. As further discussed below, this flow of blood can minimize contact of the cannula with the valve, and thus minimize injury to the valve.

A further aspect of the invention provides an assembly including a VAD and a cannula as discussed above connected to the intake of the VAD or to the discharge of the VAD.

These and other aspects of the present invention will be described in more detail below.

BRIEF DESCRIPTION OF THE DRAWINGS

These and other objects, features and advantages of the present invention will be more readily apparent from the detailed description of embodiments set forth below, taken in conjunction with the accompanying drawings, in which:

FIG. 7 is a diagrammatic view depicting a VAD in conjunction with two cannulas according to FIGS. 1-6.

FIG. 8 is a diagrammatic sectional view depicting a cannula according to a further embodiment of the invention in conjunction with an anatomical structure.

FIG. 9 is an idealized, fragmentary sectional view on an enlarged scale depicting the region indicated in FIG. 8.

FIG. 10 is a diagrammatic, partially sectional view depicting the cannula of FIG. 8 in a different orientation relative to the anatomical structure.

DETAILED DESCRIPTION

Figure 1:
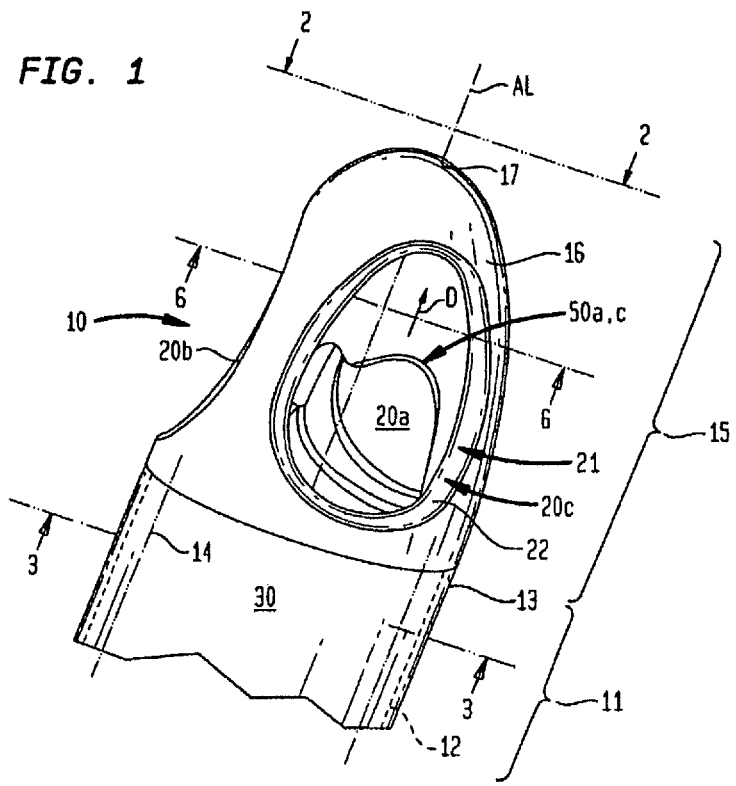
FIG. 1 is a fragmentary perspective view depicting of a cannula according to one embodiment of the present invention.

Referring to FIGS. 1-7, one embodiment of a cannula extends generally along a longitudinal axis AL. The directions along the longitudinal axis are referred to herein as proximal and distal directions. As used herein, the distal direction is the direction away from the end of the cannula which will be attached to the VAD in service, and toward the end of the cannula which will be remote from the VAD in service. For example, in the assembly of FIG. 7, a VAD 101 has an intake 103, a discharge 105 and one or more internal pumping elements (not shown) arranged to impel blood taken in through intake 103 out through discharge 105. One cannula 10A has a proximal end 111 connected to the intake 103 of the VAD and has a distal end or distal-most point 17 remote from the VAD. Another cannula 10B has its proximal end 111 connected to the discharge 105 of the VAD and has a distal end 17 remote from the VAD. In each cannula 10, direction D is the direction away from the proximal end 111. The distal direction is also indicated by arrow D in FIGS. 1, 4, and 5. The proximal direction is the opposite direction along axis AL.

Each cannula 10 includes a proximal portion 11. As best seen in FIG. 1, the proximal portion includes a wall 12 which has an outer face 13 and an inner face 14. The wall 12 extends around axis AL. The inner face 14 define a bore 30 through the proximal portion which also extends along axis AL and which extends toward the proximal end 111 (FIG. 7) of the cannula.

Face 13 extends in a smooth curve around longitudinal axis AL. Stated another way, in a cross-section of proximal portion 11 looking along axis AL, such as in FIG. 3, the line representing face 13 is a smooth, curve. In the particular embodiment depicted, face 13 is generally in the form of a circular cylinder, and hence the curve of face 13 is a circle. Likewise, inner face 14 is also in the form of a circular cylinder, and hence wall 12 has uniform dimensions in all of the radial directions perpendicular to axis AL. Wall 12 and its faces may have other cross-sectional shapes as, for example, ellipse, egg-shape, or the like. Desirably, the cross-sectional shape is a smooth curve and both faces 13 and 14 are smooth and without sharp edges, features or surfaces. In the embodiment depicted, the proximal portion 11 is of constant diameter. Stated another way, the dimensions of the proximal portion 11 perpendicular to axis AL are constant in the proximal and distal directions.

Each cannula 10 includes a distal portion 15, distal to the proximal portion 11. Distal portion 15 has outer face 16 which extends around and along axis AL. Outer face 16 may be continuous with outer face 13 of proximal portion 11. Outer face 16 tapers distally towards axis AL to the distal-most point 17. As illustrated in the Figures, the taper of outer face 16 may be, for example, parabolic, thus maintaining a smooth curve along the entire outer surface 16 and distal-most point 17. Moreover, outer face 16 has a convex, smooth, dome-like shape at distal-most point 17. The outer face 16 may alternatively have a taper that is, for example, shaped like a circle, oval or the like which may have steeper or more gentle slope than the parabolic shape illustrated in the figures. At each point along the longitudinal axis AL, outer face 16, leaving aside the openings 20 discussed below, has a cross-sectional shape which is a smooth curve around axis AL. In the particular embodiment shown, outer face 16 is a surface of revolution about longitudinal axis AL, so that as seen in cross-section viewing along the axis, as in FIG. 6, outer face forms a circular curve, interrupted only by the openings 20.

Distal portion 15 has at least two openings extending from the outer face 16 and into the interior volume of distal portion 15. In the particular embodiment shown, there are three openings 20a, 20b and 20c. Within the interior volume of distal portion 15, the openings 20a, 20b, and 20c merge with one another. The merged openings define a hollow space which communicates with bore 30 of proximal portion 11.

Figure 5:
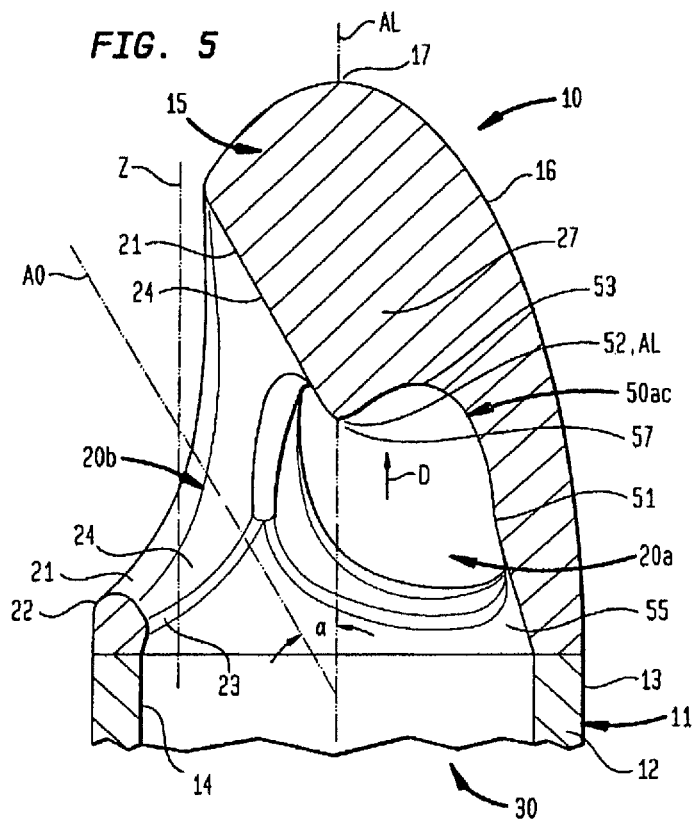
FIG. 5 is a cross-sectional view of the cannula of FIGS. 1-4, taken along line 5-5 in FIG. 2.

As best seen in FIG. 5, opening 20b extends along an individual opening axis AO. Opening 20b is generally in the form of a circular cylinder concentric with opening axis AO. The opening axis AO is oblique to axis AL, such that axis AO slopes inward, in the proximal direction, towards axis AL. In the particular embodiment depicted, opening axis AO and longitudinal axis AL define an included angle α of about 30 degrees.

Opening 20b has a bounding surface 21. Bounding surface 21 includes a cylindrical portion 24 in which the bounding surface lies at a constant distance from opening axis AO. In a portion of the opening on the distal side of opening axis AO, the cylindrical portion 24 extends substantially from outer face 16 to the point where opening 20b merges with other openings. In a portion of the opening 20b on the proximal side of the opening axis, the bounding surface 21 includes an outer portion 22 adjacent outer face 16. Outer portion 21 has a slope towards axis OA, when moving in an inward direction along axis OA towards axis AL. Also, on the proximal side of the opening axis, bounding surface 21 includes an inner portion 23, remote from outer face 16, which slopes away from axis AO when moving in an inward direction along axis AO towards axis AL. The bounding surface 21 of opening 20b desirably is substantially free of sharp angles, edges, surfaces or features.

Figure 2:
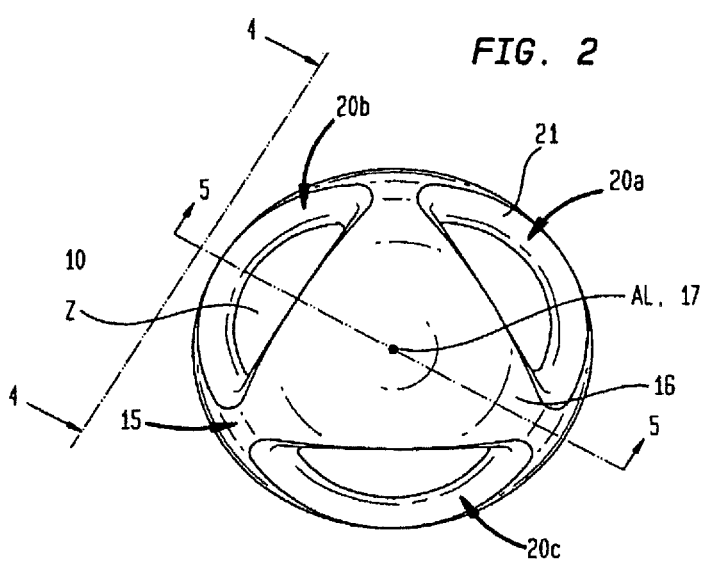
FIG. 2 is a plan view of the cannula of FIG. 1, taken along viewing line 2-2 in FIG. 1.
Figure 3:
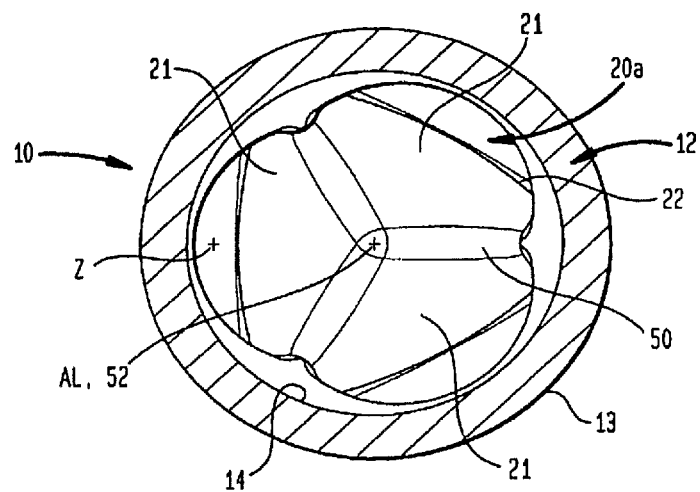
FIG. 3 is a sectional view taken along line 3-3 in FIG. 2.
Figure 4:
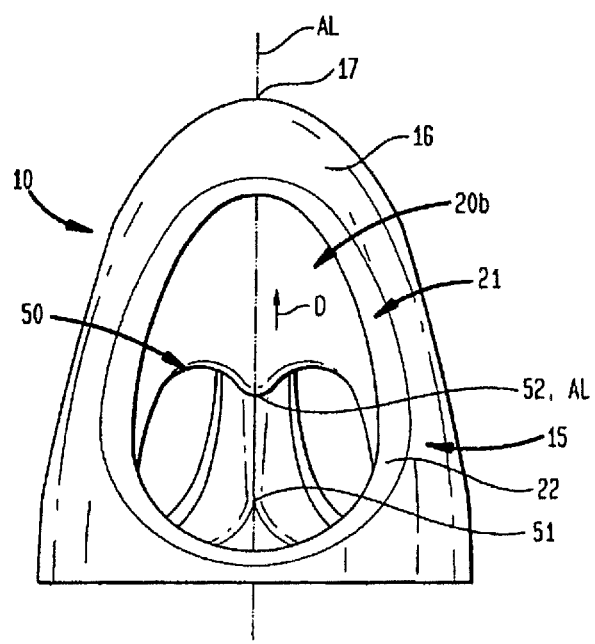
FIG. 4 illustrates a side view of the cannula of FIGS. 1-3, taken along line 4-4 in FIG. 2.

Each of the other openings 20a and 20c has the same configuration as opening 20b discussed above. As best seen in FIG. 2, the openings 20a-c are evenly spaced on outer face 16 around axis AL. Further, openings 20a-c may be positioned at the same location in the proximal and distal directions on distal portion 15. Thus, in this configuration, the openings 20a-c are uniformly spaced on distal portion 15 to form a symmetrically shaped and evenly balanced distal portion 15.

The distal portion 15 includes a solid tip 27, disposed distal to the openings 20. The proximal surface of tip 27 is defined by the bounding surfaces 21 of the openings 20.

Figure 6:
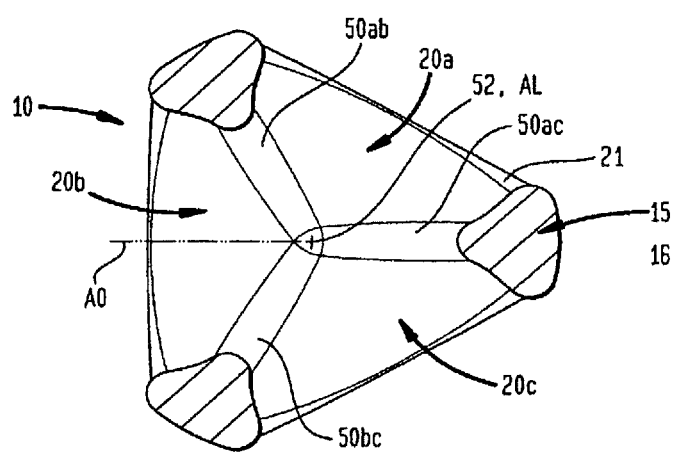
FIG. 6 illustrates a cross-sectional view of the cannula of FIGS. 1-5, taken along line 6-6 in FIG. 1.

Thus, the bounding surfaces 21 define the boundary between the hollow interior volume of distal portion 15 and the solid tip 27 of distal portion 15, as is illustrated in FIGS. 5-6.

In the embodiment depicted, the intersecting bounding surfaces 21 of mutually-adjacent openings 20a and 20c form a partial arch 50ac. In like manner, the intersecting bounding surfaces of openings 20a and 20b form another partial arch, 50ab (FIG. 6) and the intersecting bounding surfaces of openings 20b and 20c form another partial arch 50bc.

Each partial arch 50 may have a first end 51 at or near the proximal end of distal portion 15 of the cannula 10, adjacent to the proximal portion 11. The partial arch 50 may also have a second end 52 positioned on or near the axis AL. In the particular embodiment illustrated, the second end 52 is distal to the first end 51. The second ends 52 of the partial arches 50 meet at the same location on the axis AL to form a peak 57 on the axis AL, best seen in FIGS. 1 and 5. Stated another way, the solid tip 27 has a point or peak 57 pointing in the proximal direction on axis AL. Each partial arch 50 also may have an apex or distal-most point 53 positioned between the first and second ends 51 and 52 of each partial arch 50, respectively.

The distal region 15 also includes an inner tapered surface 55 which joins the inner face 14 of the proximal portion. Surface 55 slopes inwardly in the distal direction to its intersection with the bounding surfaces 21 of the openings. In the embodiment depicted, surface 55 is substantially frustoconical.

Openings 20 have substantial area for fluid flow. As referred to herein, the area of an opening is the area of the projection of the opening onto a viewing plane parallel to axis AL, such as the plane of the drawing in FIG. 4. Desirably, the aggregate area of all of the openings is greater than or the cross-sectional area of bore 30, i.e., the area of the bore as seen in a plane perpendicular to axis AL.

As best seen in FIGS. 2 and 5, in the particular embodiment depicted, each opening 20 is arranged so that at least a portion of the opening is axially aligned with bore 30. That is, an imaginary particle moving along a line Z parallel to longitudinal axis AL extending through the opening has an uninterrupted path into bore 30.

The cannula 10 may be composed of any material suitable for insertion into the body. For example, ceramics, metals, polymers, or the like may be used to manufacture or make the cannula 10 so long as the material is bio-compatible and minimally thrombogenic. Other materials may be used which may be thrombogenic, so long as a bio-compatible, non-thrombogenic coating is applied to the surface of the material. Alternatively or additionally, the material of construction, or the coating, may inhibit cell or plaque growth or attachment thereon. In the particular embodiment depicted, the material is selected so that the cannula has some flexibility. For example, the cannula may be formed from a polymer such as silicone, polycarbonate, urethane with silicone, polystyrene-polyisobutylene-polystyrene (SIBS), and may have a flexible reinforcement such as a spiral-wound wire in the proximal portion. The cannula may include radioopaque materials so that the position of the cannula can be detected in X-ray based imaging techniques such as conventional X-ray imaging, fluoroscopic imaging, CAT scanning and the like. The radioopaque materials can be in the form of discrete markers positioned at known locations on the cannula. Alternatively or additionally, the materials of construction of the cannula may be radioopaque, as for example, polymers can be rendered radioopaque by dispersing certain metallic compounds in the polymers. Alternatively or additionally, the cannula may include discrete markers or dispersed materials which can be detected by other imaging modalities. For example, gadolinium-containing materials can be detected readily in some magnetic resonance imaging procedures, with good contrast to the surrounding tissues.

In the embodiment depicted in FIG. 7, one cannula 10A as discussed above is attached to the intake 103 of a VAD 101, so that the bore 30 of the proximal portion communicates with the intake 103 of the VAD. Thus, this cannula 10A serves as the intake cannula on the VAD. The distal portion 15 of cannula 10A serves as the intake region. The VAD and cannula 10A may be positioned such that at least a portion of the cannula 10A, which includes the distal portion 15, is positioned within a chamber in the heart, typically within a ventricle.

Cannula 10B, which is identical to cannula 10A, is connected to the discharge 105 of the VAD, and thus serves as a discharge cannula. The distal portion 15 of cannula 10B forms the discharge region. The distal portion or discharge region of cannula 10B is positioned in an artery, most commonly in the aorta.

The cannula discussed herein can be used with any VAD. Depending on the design of the VAD and the application, only one cannula can be used as an intake cannula or discharge cannula. For example, where the intake of the VAD is positioned within the ventricle, an intake cannula may not be required. Where the discharge of the VAD is disposed within the aorta or other artery, a discharge cannula maynot be required.

The design of the distal portion 15, of the cannula is believed to promote stability of the distal portion during use, and to minimize movement of the distal portion caused by the flow of blood into or out of the cannula. In particular, it is believed that the flow of blood with a radial component of velocity tends to hold the distal portion of the cannula away from neighboring solid tissues such as the wall of an artery or the heart wall. For example, where the cannula is used as an outflow cannula, the flow of blood with a radially outward component of velocity is believed to have this effect. Depending on the application and on the stiffness of the cannula, the stability of the distal portion may allow positioning of the cannula without the need for auxiliary devices to hold the cannula away from the wall of the heart or artery. Moreover, even if the cannula rests against the wall of the heart or artery, it will not be blocked; at least one opening 20 typically will remain open. Also, the distal portion minimizes flow resistance through the intake or discharge region 15 of the cannula 10, and thus may alleviate turbulence and eddying. The smooth bounding surfaces 21 of openings 20 also help to minimize turbulence and eddying of blood passing through the openings.

The smooth outer faces 13 and 16, and tapered distal portion 15, facilitate insertion of cannula 10, and help to assure that cannula 10 does not damage the surrounding body tissue. In particular, the tapered and rounded distal portion 15 is believed to contribute to the ease of insertion. The convex, smooth, dome-like shape at distal-most point 17 is believed to contribute to ease of insertion. The taper of distal portion 15 may act as a distracter to safely separate the surrounding tissue during insertion.

Numerous variations of the features discussed above may be used. For example, the embodiments discussed above have only a single bore in the proximal section. The bore can be subdivided to provide a multi-lumen cannula, in which different lumens communicate with different openings 20.

The number of openings may be varied as, for example, to use two or four openings or more. The dimensions of the cannula may be selected according to the required flow volume. Merely by way of example, a cannula for carrying about 5 l/min of blood has a bore 30 of about 6 mm interior diameter. The slopes of bounding surface 21 may be varied. The bounding surfaces discussed above are well-suited for use either as an intake cannula or a discharge cannula.

The cannula discussed above can be employed with devices other than VADs, as for blood circulation systems such as heart-lung machines, dialysis systems and the like.

A cannula 110 according to a further embodiment of the invention (FIGS. 8 and 9) has a proximal end 121, a distal region 115, and a proximal region 111 extending from the distal region 115 towards the proximal end 121. The cannula is provided with openings 120, which desirably are positioned in or near the distal region 115. The cannula has a bore 130 extending through the proximal region 111 and communicating with the openings 120. Merely by way of example, these features may be similar to the corresponding features of the cannulas discussed above with reference to FIGS. 1-7.

Cannula 110 also has ports 101 extending through the wall 112 of the cannula in the proximal region 111. Stated another way, ports 101 are disposed proximally of openings 120. Ports 101 extend between the bore 130 of the cannula and the outer surface 113 of the proximal region of the cannula. The ports may be spaced apart from one another around the circumference of the cannula, and also may be spaced apart along the axial length of the proximal region. In the embodiment depicted, the ports are provided in a few rows spaced axially from one another, so that the ports 101 are distributed over only a small portion of the axial length of the proximal region 111. Although the ports 101 are depicted as regularly spaced, circular holes, this is not essential. The ports 101 may be irregularly shaped, irregularly spaced, or both. For example, the wall 112 of the proximal section may incorporate a section formed from a porous material having numerous very small pores which constitute ports 101. The ports 101, in the aggregate, desirably have flow resistance which is substantial in comparison to the flow resistance of the openings 120 in aggregate. As used in this disclosure, the "flow resistance" of the ports in the aggregate means the number obtained by dividing the ΔP by the total flow of blood per unit time through the ports, where ΔP is the difference between the pressure within the bore and the pressure outside of the cannula. Likewise, the flow resistance of the openings in the aggregate is the number obtained by dividing ΔP by the total flow of blood per unit time through the openings. Thus, when the cannula is used as a discharge cannula as depicted in FIGS. 8 and 9, a substantial portion of the blood flowing into the proximal end 121 of the cannula flows out of the cannula through the openings 120. For example, the aggregate flow resistance of ports 101 may be greater than the aggregate flow resistance of openings 120, so that the majority of the blood will be discharged through openings 120. In some embodiments, the ratio of the aggregate flow resistance of ports 101 to the aggregate flow resistance of openings 120 is 5:1 to 10:1 or more, so that the openings 120 carry about 80% to 90% or more of the blood flowing into the proximal end 121.

In use, the cannula 110 is positioned to extend through a valve V of the circulatory system. For example, valve V may be the mitral valve, tricuspid valve, aortic valve or other valve of the heart, or may be a valve in a blood vessel. Valve V has a plurality of leaves L, two of which ($L_1$ and $L_2$) are depicted in FIG. 8. The valve is arranged to open so as to accommodate natural blood flow in a forward or downstream direction indicated by arrow $F_N$ in FIG. 8. When the valve is open to accommodate a pulse of blood flow, leaves $L_1$ and $L_2$ move away from one another as indicated in broken lines at $L_1'$ and $L_2'$ in FIG. 8. When the pressure of blood downstream from the valve (below the valve in FIG. 8) is above the pressure upstream of the valve, the pressure urges leaves $L_1$ and $L_2$ back to a closed position in which the leaves abut one another so that the valve closes to block retrograde flow. Cannula 110 is positioned so that the portion of proximal region 111 having ports 101 is disposed in alignment with the valve V. When valve V is urged to the closed condition, leaves $L_1$ and $L_2$ are urged towards the outer surface 113 of the cannula. However, the blood flowing outwardly through the ports 101 tends to keep the leaves slightly away from the surface of the cannula. This tends to minimize damage to the valve caused by repeated or prolonged contact with the cannula.

As depicted in FIG. 8, the cannula is positioned for forward flow, so that the direction of flow through the cannula is the same as the direction of natural forward or downstream flow $F_N$. Thus, the distal region and openings 120 are positioned on the downstream side of valve V. As shown in FIG. 10, the cannula may be positioned in the opposite direction, with openings 120 on the upstream side of the valve, to provide retrograde flow. In this arrangement as well, discharge of blood through ports 101 acts to protect the leaves of the valve and limit or eliminate contact with the cannula. The ports 101 may be provided in cannulas having outlets and distal regions configured differently from those discussed above with reference to FIGS. 1-7.

Although the invention herein has been described with reference to particular embodiments, it is to be understood that these embodiments are merely illustrative of the principles and applications of the present invention. It is therefore to be understood that numerous modifications may be made to the embodiments disclosed herein and that other arrangements may be devised without departing from the spirit and scope of the present invention as defined by the appended claims.

The invention claimed is:

1. A blood circulation assembly, comprising:
   a blood circulation device having an inlet and a discharge;
   a first cannula including a proximal portion coupled to and in communication with the inlet, the proximal portion having a wall extending around a first longitudinal axis and having outer and inner faces, said inner face defining a bore, and a distal portion defining an intake region including an outer face tapering distally toward said axis and at least two openings extending from said outer face and merging with one another to form a hollow space within said distal portion, said hollow space communicating with said bore of said proximal portion; and
   a second cannula including a proximal portion coupled to and in communication with the discharge, the proximal portion having a wall extending around a first longitudinal axis and having outer and inner faces, said inner face defining a bore, and a distal portion defining a discharge region including an outer face tapering distally toward said axis and at least two openings extending from said outer face and merging with one another to form a hollow space within said distal portion, said hollow space communicating with said bore of said proximal portion, and the distal portion of the first cannula and the distal portion of the second cannula defining a blood flow path therebetween, wherein said at least two openings of the first and second cannulas have a smooth curved bounding surface which continues from said respective outer face of said respective distal portion to said respective hollow space of said respective distal portion, and wherein over at least a portion of each of said at least two openings of the first and second cannulas, an outer portion of said bounding surface, adjacent said outer face of said respective distal portion, slopes towards an opening axis in an inward direction along said opening axis toward said respective longitudinal axis and an inner portion of said bounding surface remote from said respective outer face slopes away from said opening axis in the inward direction.

2. The assembly of claim 1, wherein the blood circulation device is adapted to impel blood taken in through said intake out through said discharge.

3. The assembly of claim 1, wherein said distal portion of each of the first and second cannulas has a solid portion from a distal-most point of said respective distal portion to said bounding surfaces of said at least two openings.

4. The assembly of claim 1, wherein the outer face of the distal portion of each of the first and second cannulas is continuous with the outer face of the respective proximal portion.

5. The assembly of claim 4, wherein said proximal and distal portions of the first and second cannulas have a circular cross-sectional shape.

6. The assembly of claim 1, wherein said proximal portion of each of the first and second cannulas has dimensions transverse to said respective longitudinal axis, said dimensions being constant in the proximal and distal directions.

7. A blood circulation assembly, comprising:
a blood circulation device having an inlet and a discharge;
a first cannula including a proximal portion coupled to and in communication with the inlet, the proximal portion having a wall extending around a first longitudinal axis and having outer and inner faces, said inner face defining a bore, and a distal portion defining an intake region including an outer face tapering distally toward said axis and at least two openings extending from said outer face and merging with one another to form a hollow space within said distal portion, said hollow space communicating with said bore of said proximal portion; and
a second cannula including a proximal portion coupled to and in communication with the discharge, the proximal portion having a wall extending around a first longitudinal axis and having outer and inner faces, said inner face defining a bore, and a distal portion defining a discharge region including an outer face tapering distally toward said axis and at least two openings extending from said outer face and merging with one another to form a hollow space within said distal portion, said hollow space communicating with said bore of said proximal portion, and the distal portion of the first cannula and the distal portion of the second cannula defining a blood flow path therebetween, wherein each of said openings of the first and second cannulas extend along an opening axis that is oblique to said respective longitudinal axis and slopes inward towards said respective longitudinal axis in a respective proximal direction.

8. The assembly of claim 7, wherein said bore of said first cannula is connected to said inlet of said blood circulation device whereby said first cannula serves as the intake region for blood flowing into the blood circulation device and said bore of said second cannula is connected to said discharge of said blood circulation device whereby said second cannula serves as the discharge region for blood flowing from the blood circulation device.

9. A blood circulation assembly, comprising:
a blood circulation device having an inlet and a discharge;
a first cannula including a proximal portion coupled to and in communication with the inlet, the proximal portion having a wall extending around a first longitudinal axis and having outer and inner faces, said inner face defining a bore, and a distal portion defining an intake region including an outer face tapering distally toward said axis and at least two openings extending from said outer face and merging with one another to form a hollow space within said distal portion, said hollow space communicating with said bore of said proximal portion; and
a second cannula including a proximal portion coupled to and in communication with the discharge, the proximal portion having a wall extending around a first longitudinal axis and having outer and inner faces, said inner face defining a bore, and a distal portion defining a discharge region including an outer face tapering distally toward said axis and at least two openings extending from said outer face and merging with one another to form a hollow space within said distal portion, said hollow space communicating with said bore of said proximal portion, and the distal portion of the first cannula and the distal portion of the second cannula defining a blood flow path therebetween, wherein at least a portion of each said opening of the first and second cannulas, at said outer face, being axially aligned with the respective hollow space and the respective bore such that a straight line extending through the opening parallel to the respective longitudinal axis has an uninterrupted path into the respective hollow space, the respective bore and the inlet or discharge of the blood circulation device.

10. A blood circulation assembly, comprising:
a blood circulation device having an inlet and a discharge;
a first cannula including a distal portion defining an intake region and having an outer face tapering distally toward a first longitudinal axis of the first cannula and a hollow space, and a proximal portion coupled to the inlet and having a wall extending around the first longitudinal axis and having outer and inner faces, said inner face defining a bore, the bore being in communication with said hollow space and said inlet, the outer face of the distal portion is continuous with the outer face of the proximal portion; and
a second cannula including a distal portion defining a discharge region and having an outer face tapering distally toward a second longitudinal axis of the second cannula and a hollow space, and a proximal portion coupled to the inlet and having a wall extending around the second longitudinal axis and having outer and inner faces, said inner face defining a bore, the bore being in communication with said hollow space and said discharge, the outer face of the distal portion is continuous with the outer face of the proximal portion, and the distal portion of the first cannula and the distal portion of the second cannula define a blood flow path therebetween, wherein the distal portion of the first cannula includes at least two openings extending from said outer face and merging with one another to form the hollow space such that at least a portion of each opening, at said outer face, is axially aligned with the hollow space and the bore such that a straight line extending through the opening parallel to the first longitudinal axis has an uninterrupted path into the respective hollow space, the respective bore and the inlet of the blood circulation device.

11. The assembly of claim 10, wherein the distal portion of each of the first and second cannulas includes at least two openings extending from said respective outer face and merging with one another to form said respective hollow space, the at least two openings of each cannula have a smooth curved bounding surface which continues from said respective outer face of said respective distal portion to said respective hollow space of said respective distal portion.

12. The assembly of claim 11, wherein each of said openings on the first and second cannulas extend along a particular opening axis that is oblique to said respective longitudinal axis and slopes inward towards said respective longitudinal axis in a respective proximal direction such that over at least a portion of each of said openings, an outer portion of said bounding surface, adjacent said outer face of said respective distal portion, slopes towards the opening axis in an inward direction along said opening axis toward said respective longitudinal axis and an inner portion of said bounding surface remote from said respective outer face slopes away from said opening axis in the inward direction.

13. The assembly of claim 10, wherein said bore of said first cannula is connected to said inlet of said blood circulation device whereby said first cannula serves as the intake region for blood flowing into the blood circulation device and said bore of said second cannula is connected to said discharge of said blood circulation device whereby said second cannula serves as the discharge region for blood flowing from the blood circulation device.

* * * * *